(12) United States Patent
Merkel et al.

(10) Patent No.: US 6,456,093 B1
(45) Date of Patent: Sep. 24, 2002

(54) APPARATUS AND METHOD FOR DETECTION OF FOREIGN BODIES IN PRODUCTS

(75) Inventors: Harald Merkel, Kållered; Mikael Reimers, Västra Frölunda; Christina Skjöldebrand, Saltsjö-Boo, all of (SE)

(73) Assignee: SIK - Institut för livsmedel och biotecknik AB, Göteborg (SE)

( * ) Notice: Subject to any disclaimer, the term of this patent is extended or adjusted under 35 U.S.C. 154(b) by 0 days.

(21) Appl. No.: 09/506,832

(22) Filed: Feb. 18, 2000

(30) Foreign Application Priority Data

Sep. 17, 1999 (SE) ................................ 9903348

(51) Int. Cl.[7] ............................................. G01R 27/32
(52) U.S. Cl. ..................................................... 324/640
(58) Field of Search ............................ 324/640, 639, 324/642, 637, 96

(56) References Cited

U.S. PATENT DOCUMENTS

| 4,326,163 | A | | 4/1982 | Brooke |
| 5,333,493 | A | * | 8/1994 | Cutmore ............... 324/640 |
| 5,845,529 | A | * | 12/1998 | Moshe et al. .......... 324/640 |
| 4,805,627 | A | | 2/2000 | Klingenbeck et al. |

FOREIGN PATENT DOCUMENTS

| DE | 4311103 A1 | 10/1994 |
| DE | 29719600 U1 | 2/1998 |
| SE | 8403438-8 | 4/1987 |
| SE | 512315 C2 | 2/2000 |
| WO | 9621153 | 7/1996 |
| WO | WO9621153 | 7/1996 |

OTHER PUBLICATIONS

Shigeru Nakayama, Abstract JP 6 3,285,487, Nov. 22, 1988.

* cited by examiner

Primary Examiner—N. Le
Assistant Examiner—J Kerveros
(74) Attorney, Agent, or Firm—Birch, Stewart, Kolasch & Birch, LLP

(57) ABSTRACT

The present invention relates to an apparatus for detection of foreign bodies in materials, comprising a first antenna device for transmitting electromagnetic signals, the transmitted electromagnetic signals are in the microwave range, the signals comprise at least two signals at different frequencies, a second antenna device for receiving signals originating from the first antenna, where the received signals, at least partially, passes through the materials, device for measuring at least one parameter of the received signals for each frequency, so as to obtain parameter values, device for comparing the parameter value with the corresponding output parameter value of the transmitted signals, so as to obtain a comparison value for each of the frequencies, device for analyzing each comparison value based on a reference value, which reference value is accessible to the apparatus, and device for emitting a signal when the comparison value differs a predetermined amount from the reference value. The invention also relates to a method for detection of foreign bodies in materials.

26 Claims, 2 Drawing Sheets

APPARATUS AND METHOD FOR DETECTION OF FOREIGN BODIES IN PRODUCTS

TECHNICAL FIELD

The present invention relates to an apparatus for detection of foreign bodies in products, especially in food products. The invention also relates to a method using said apparatus.

Furthermore, the present invention relates to an apparatus for detection of changes in material properties and contents in a product, especially detection of voids, defects and inhomogeneities within a material. The invention also relates to a method using said apparatus.

BACKGROUND OF THE INVENTION

Intensive efforts to improve product quality are presently undertaken within the food industry, such as reducing the probability of products containing foreign bodies to reach the consumer market.

The term foreign bodies comprises all solid materials that are undesired in food products, originating from the product or not, such as bone fragments, bits of glass, rubber, gravel/stone, hair, insects, etc. Present techniques to detect some classes of foreign bodies in food products are very expensive and/or can only detect some foreign bodies, such as magnetic bodies, bodies with deviating color and size or bodies with deviating weight. Examples of such techniques are ocular examination and X-ray detection.

In the Japanese Patent JP 63285487, by Shigeru, a detection method of metal in foodstuff is disclosed. The purpose of the invention is to detect metal powder, irrespective of the shape and size of the foodstuff by irradiating metal contaminated foodstuff with microwaves in order to generate an electric discharge, which discharge is detected.

In WO 96/21153, by Hoskens et al., an apparatus for determining the qualities of an irradiatable body by means of penetrating radiation is disclosed, where said radiation could be of any wavelength. The apparatus comprises a device for parallel radiation from one side of a irradiable body, a device for receiving the radiation leaving the body and deriving a transmission signal therefrom, and means for deriving from the transmission signal information concerning the qualities of the irradiated body, such as bone tissue in pieces of meat.

From information derived from the transmission signal the mass of the inspected body is determined, the mass of the body is a function of height and density and a correlation exists between mass and radiation attenuation, thus a presence of possible inhomogeneities may be detected.

A problem encountered with the prior art is that it is impossible, or very difficult, to detect a multitude of different types of foreign bodies in products. Metal or particles with high density are easy to detect in a product containing material with low density, but foreign bodies embedded in a material with a similar density are difficult to detect.

A further problem with present techniques is that it is difficult to achieve on-line detection of foreign bodies on a completed product in production, which means that the detecting method has to be fast, non-invasive and non-destructive.

SUMMARY OF THE INVENTION

A first object with the invention is to provide an apparatus and a method for detection of foreign bodies in products, especially food products, which overcome the above mentioned problems.

The first object is achieved by an apparatus for detection of foreign bodies in a material, comprising a first antenna device for transmitting electromagnetic signals in the microwave range, the signals comprise at least two signals at different frequencies; a second antenna device for receiving signals originating from the first antenna, the received signals, at least partially, pass through the material; means for measuring at least amplitude and phase information of the received signals for each separate frequency, so as to obtain a plurality of parameter values; means for comparing each parameter value with the corresponding amplitude and phase information of the transmitted signals, so as to obtain a comparison value for each of the separate frequencies; means for analyzing each comparison value based on a reference value, which reference value is accessible to the apparatus; and means for emitting a signal when the comparison value differs a predetermined amount from the reference value.

Further, the first object is achieved by a method for detection of foreign bodies in a product comprising transmitting electromagnetic signals from a first antenna device, said transmitted electromagnetic signals being in the microwave range, said signals comprise at least two signals at different frequencies; receiving signals in a second antenna device originating from said signals transmitted from said first antenna device, where said received signals, at least partially, have passed through said product; storing reference values comprising amplitude and phase information for each transmitted separate frequency in a memory; measuring at least amplitude and phase information of said received signals for each separate frequency, so as to obtain parameter values; comparing the parameter values with the corresponding amplitude and phase information of said transmitted signals, so as to obtain a comparison value for each of said frequencies; analyzing each comparison value using one of said reference values from said memory; and emitting a signal when said comparison value differs a predetermined amount from said reference value.

A second object with the invention is to provide an apparatus and a method for detection of changes in material property and content in materials.

The second object is achieved by an apparatus for detection of changes in material properties and contents in a product, comprising a first antenna device for transmitting electromagnetic signals in the microwave range, said signals comprise at least two signals at different frequencies; a second antenna device for receiving signals originating from said first antenna, said received signals, at least partially, pass through said product; means for measuring at least amplitude and phase information of said received signals for each separate frequency, so as to obtain parameter values; means for comparing each parameter value with the corresponding amplitude and phase information of said transmitted signals, so as to obtain a comparison value for each of said separate frequencies; means for analyzing each comparison value based on a reference value, which reference value is accessible to said apparatus; and means for emitting a signal when said comparison value differs from a predetermined amount from said reference value.

Further the second object is achieved by a method for detection of changes in material properties and contents in a product comprising the steps of transmitting electromagnetic signals from a first antenna device, said transmitted electromagnetic signals being in the microwave range, said signals comprise at least two signals at different frequencies; receiving signals in a second antenna device originating from said signals transmitted from said first antenna device, where said received signals, at least partially, have passed through said product; storing reference values comprising amplitude and phase information for each transmitted different frequency in a memory; measuring at least amplitude and phase information of said received signals for each frequency, so as to obtain parameter values; comparing the parameter values with the corresponding amplitude and phase information of said transmitted signals, so as to obtain a comparison value for each of said frequencies; analyzing each comparison value using one of said reference values from said memory; and emitting a signal when said comparison value differs a predetermined amount from said reference value.

An advantage with the present invention is that a large variety of foreign bodies is detectable in a product.

Another advantage is that the present invention allows fast measurement, detection and evaluation.

Still another advantage is that the present invention is cheap and easy to implement and can be integrated in existing production facilities.

Still another advantage is that the present invention allows to detect foreign bodies in products after final processing, in a non-destructive manner.

Yet another advantage is that the invention provide an apparatus and a method for detecting deviations of the material properties and contents of a product, or material, provided that the product comprises two components having different dielectric constants.

DETAILED DESCRIPTION OF PREFERRED EMBODIMENTS

Figure 1:
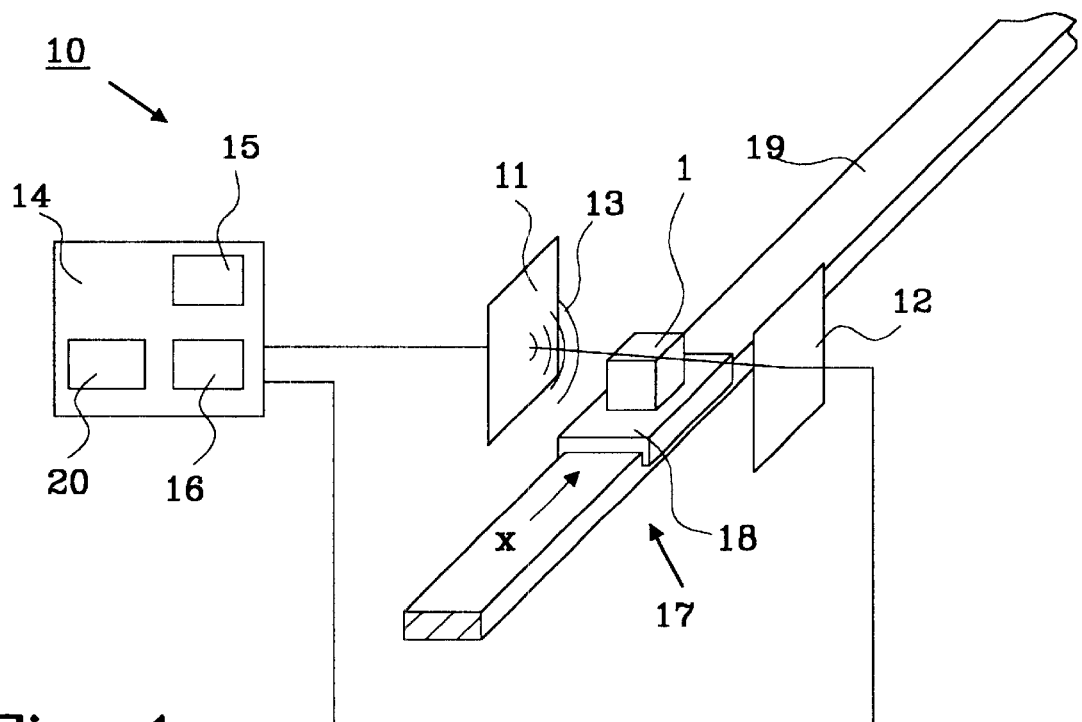
FIG. 1 shows an apparatus according to the present invention.

FIG. 1 shows an apparatus 10 for detection of foreign bodies in a product 1 according to the present invention. The inventive apparatus comprises a first antenna device 11, a second antenna device 12, where said first antenna device 11 transmits electromagnetic signals 13' in the microwave range. The transmitted signals 13' are arranged to, at least partially, pass through the product 1, which is under examination. After the signals have passed through the material 1 the signals 13" are received at said second antenna device 12.

Figure 2:
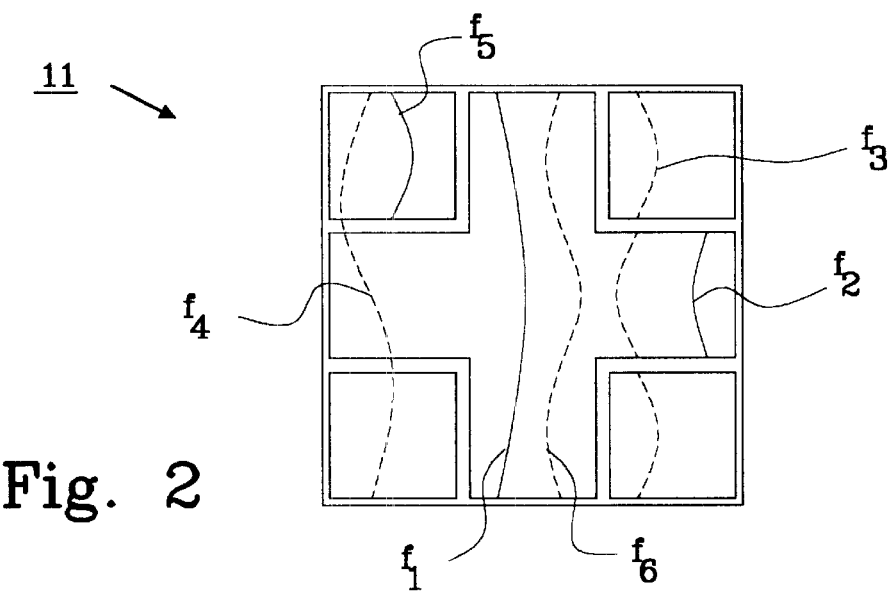
FIG. 2 shows an antenna device, which may be used in the apparatus in FIG. 1.

The first and second antenna device 11, 12 transmits and receives signals having at least two separate frequencies, preferably more, e.g. 400, different separate frequencies in several contiguous frequency blocks furthermore referred to as frequency channels. The antenna devices, which are described in more detail in FIG. 2, are connected to a microwave circuit 14, such as a network analyser. The microwave circuit 14 comprises a microwave oscillator 15, which feeds signals 13' to be transmitted to the first antenna device 11, and a microwave measuring system 16, e.g. a vector voltmeter, which collects and measure certain parameters, such as amplitude $|A|$ and/or phase $\psi$, of the received signals 13" from the second antenna device 12.

The product 1 which is under examination is preferably placed on a transportation system 17 comprising, for instance, a carrier 18 on a conveying equipment 19, a conveyor belt, a vertical pipe with flowing products or the like.

In the described preferred embodiment, the products pass through a gap between the first 11 and the second 12 antenna device, to allow the transmitted signals to, at least partially, pass through the whole of said product. The product 1, which is placed on the carrier 18, is moved through the open space by means of, for instance, a motor driven cart. Signals having pre-selected number of frequencies in the microwave range, in one or more frequency channels, are transmitted from said first antenna device, and are received at said second antenna device to be measured in the network analyser 14. A new measurement is performed after a predetermined time interval, during which the product has moved a distance in a first direction x.

The antenna devices comprise at least one frequency channel within which channel at least two separate frequencies may be transmitted. This may be implemented using a separate antenna, or antenna section, for each frequency channel, where the frequency of each transmitted signal within each frequency channel may be controlled by the microwave oscillator 16.

A preferred embodiment of a first antenna device 11 is shown in FIG. 2, which transmits signals in a plurality of frequency channels, $f_1$–$f_6$. This type of antenna is a patch antenna with capacitively coupled patches. The mid frequency for each frequency channel could be as presented in table 1.

This type of patch antenna is cheap to manufacture and simple to control to achieve the desired number of channels, each channel being controllable to contain at least two signals with separate frequencies. The second antenna device 12 comprises the same features as the first antenna device 11 for reception of the transmitted signals.

TABLE 1

A schematic layout of the wave pattern of the centre frequencies is illustrated in FIG. 2 as dashed lines with reference to the different channels $f_1$–$f_6$ in table 1.

| Channel | Frequency [GHz] |
|---|---|
| $f_1$ | 1.45 |
| $f_2$ | 3.2 |
| $f_3$ | 4.1 |
| $f_4$ | 4.5 |
| $f_5$ | 5.2 |
| $f_6$ | 5.8 |

By using this type of antenna device 11, in the above described apparatus 10, information containing the dielectric function can be obtained in an examined product as a function of said first direction x, and said selected frequencies.

It is essential to have at least two signals with separate frequencies within at least one frequency channel to reach the above mentioned information regarding the dielectric constant, according to the invention. This will come more apparent in the following.

The basic theory behind the invention is to detect differences, such as foreign bodies, contamination, damages (cracks etc.), causing a change in the dielectric constant of the examined product. This is done by transmitting signals, at least partially, through said product, which in it self must, at least partially, consist of a dielectric substance.

Parameter values from said parameters, such as amplitude $|A|$ and/or phase $\psi$, which are used for determining the dielectric constant of the examined product, are measured in said microwave measuring system 16. The measured parameter values are compared with the corresponding values of the transmitted signals, so as to obtain a comparison value for each frequency in each frequency channel.

Each comparison value is then compared with a reference value, which is available to the microwave circuit 14, e.g. stored in a memory 20 in said microwave circuit 14. Reference values are preferably obtained by measuring parameters from received signals that have passed through a reference sample of the examined type of product, which reference sample is free from any foreign bodies or other defects that will cause a change of the properties of the microwave transmission through the product as described by the profile of the dielectric function as a function of frequency.

Sometimes it is difficult to obtain a "clean" reference sample and, therefore, the reference values are preferably obtained by measuring parameter values of a plurality of products, and calculate statistics, such as an average, for each parameter value and use that as a reference value for each frequency. A typical number of products, measured to obtain said calculated reference value, is approximately 100 products.

Alternatively reference values may be obtained evaluating a model for the microwave transmission through the product and the transmit and receive properties of the antennas 11 and 12.

Figure 3:
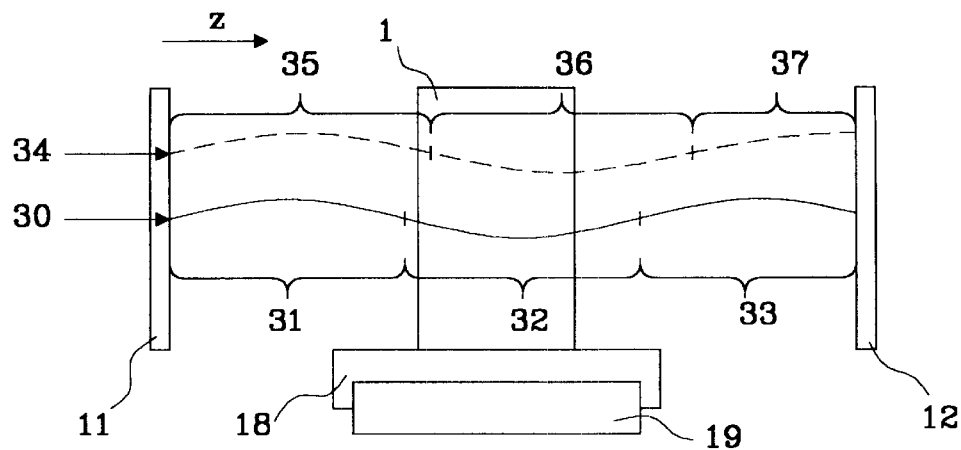
FIG. 3 shows a side view of an antenna arrangement according to the present invention.

FIG. 3 shows a side view of the measurement gap where the examined product 1 passes through. On the left side of the product is the first antenna device 11 arranged and on the right side is the second antenna device 12 arranged. A signal 30 is transmitted from said first antenna device 11, and received by said second antenna device 12. The received signal as a function of x, s(x), may be expressed by:

$$s(x)=|A|e^{i\psi},$$

where $|A|$ is the amplitude and $\psi$ is the phase of the received signal. The phase $\psi$ is proportional to:

$$\psi = k_z \cdot z + 2\pi n,$$

where z is the distance between the first and the second antenna device 11, 12, $k_z$ is the propagation constant in the z direction, and n is an integer number and stands for the number of completed trains in the gap. The propagation constant is in turn equal to:

$$k_z = \omega \sqrt{\in \mu},$$

where $\omega$ is the angular frequency of the microwave signal related to the frequency of the microwave signal f by: $\omega=2\pi f$. $\in(\omega)$ is the equivalent dielectric function and $\mu$ is the equivalent permeability of the material in the specific measurement gap. By transmitting a single signal there is a possibility to determine the absolute value of the amplitude and the phase shift of the received signal, but it is impossible to uniquely determine the equivalent dielectric function, since phase measurements allow only the determination of the modulus of the wave trains by 360 degrees. Therefore the integer number of completed wave trains within the measurement gap is not known from a single measurement.

Figure 4:
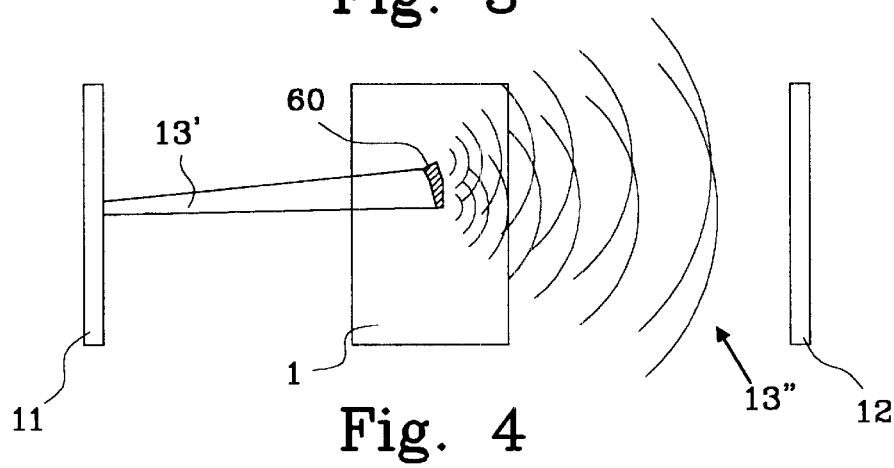
FIG. 4 shows a side view of an antenna arrangement, as in FIG. 2, illustrating diffraction/scattering in an examined product.

In FIG. 3 there is shown a first transmitted signal 30, drawn with a continuous line, having two complete oscillation periods 31, 32, preceding the last not complete period 33. By adding a second signal 34, drawn with a dashed line, in a different frequency compared to the first signal 30, having two complete oscillation periods 35, 36, preceding the last not complete period 37, the propagation time may be determined by plotting the equivalent dielectric function assuming different number of oscillation periods, as is shown in FIG. 4.

In an examined product, the equivalent dielectric function is unknown, but may be expressed as a known part, $\in_{product}(\omega,\xi)$, belonging to the clean product and an unknown part, $\in_{foreign\ body}(\omega,\xi)$, belonging to the microwave transmission properties of the foreign body. The equivalent dielectric function of the foreign body contains scattering, diffraction, absorption, reflection and transmission effects of the foreign bodies. Therefore it depends strongly on frequency $\omega$ (since diffraction lobes shift with frequency) and with the angle of observation $\xi$ (if sharp edges are present). The measured transmitted signal may therefore be broken down in the following form involving $\eta$, describing the abundancy of foreign bodies in the product where $\eta=0$ indicates no foreign body to be present:

$$\in_{tot} = (1-\eta) \cdot \in_{product} + \eta \cdot \in_{foreign\ body}, \quad (I)$$

where $\eta$ varies between 0 and 1, depending on the amount of foreign bodies present in the examined product.

The amplitude $|A|$ and phase $\psi$ of the transmitted microwave signal $S_{21}$ is measured for all frequencies and for each displacement x resulting in a two dimensional graph of a complex variable $(S_{21}=|A|\exp[i\psi])$, where changes in the products composition easily can be detected.

FIG. 4 illustrates what happens when a signal 13' is transmitted from said first antenna device 11, through a product 1. Inside said product, there is a small piece of a foreign body 60, such as metal, stone, etc., disturbing the signal on its way to the receiving antenna device 12. The received signal 13" will in this case be subject to diffraction or scattering causing an interference pattern to arise. This will mainly be detectable as a characteristic pattern in the amplitude $|A|$ frequency.

The main task of the signal processing part is the appropriate filtering of the data and the definition of a threshold value enabling to discern contaminated from non-contaminated products minimising the estimator errors in both directions, i.e. (1) assigning a foreign body to a pure product and (2) letting a contaminated product pass. Obviously some tolerances at (1) is given whereas (2) must be reduced as far as possible. For simple classes of products and foreign bodies (i.e. homogenous, wet products and dry foreign bodies) it is sufficient to apply equation (I) directly and replace the equivalent dielectric function of the pure product by measured data from a pure product and calculating the difference between the measured reference and measured product. If the mean square of the residual does not exceed a certain threshold, the product is considered ok, otherwise it is rejected.

Figure 5A:
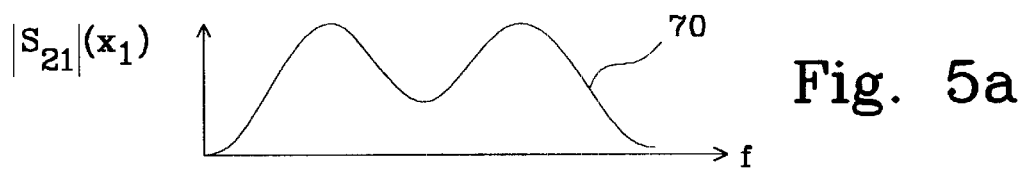
FIGS. 5a–5c shows a method to extract information regarding diffraction measurements, according to the present invention.
Figure 5B:
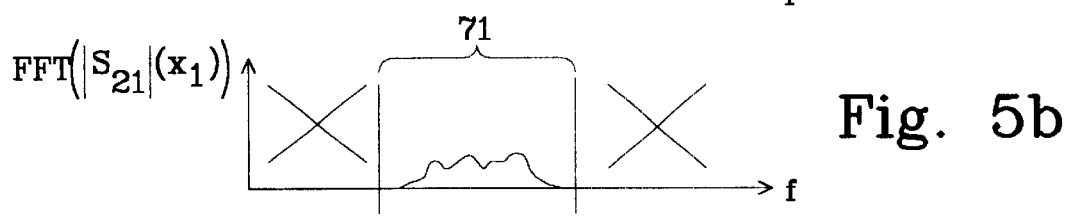
Figure 5C:
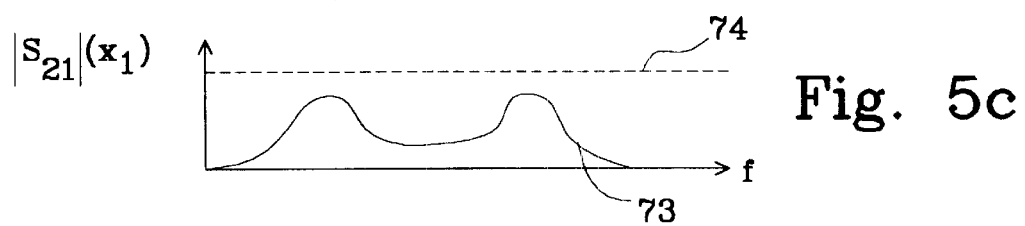

FIGS. 5a–5c illustrates how a useful value may be obtained using especially the information contained in the diffraction patterns. FIG. 5a shows the damping value $|S21|$ for a specific displacement x=x1 for a multiple of frequencies f, resulting in a curve 70. By applying a "Fast Fourier Transform" (FFT) on the damping $|S21|$ a result is obtained, as shown in FIG. 5b. This result is subject to suitable filtering techniques to select a window 71 where the desired information is contained. These types of filtering techniques are well known to a skilled person within the technical field and are, thus, not described in more detail in this application.

FIG. 5c shows the resulting curve 73 after a retransformation of the filtered FFT-spectrum in FIG. 5b back to the damping $|S_{2,1}|(x_1)$ as a function of frequency f. A threshold value 74 is also indicated, where values lower than the threshold value for each frequency is allowed, and, accordingly, values higher than the threshold is unacceptable and renders an alarm signal from the microwave circuit 14, where the FFT treatment is performed.

The above described apparatus and method for detecting foreign bodies in material, may also be used within the area of monitoring and detecting changes in material property and content, provided said material comprises at least two different components having different dielectric constants. An example of such a material is a material having a void within the material, such as a plastic part having an air bubble inside. These types of defects are easily detected by using the inventive apparatus and method.

What is claimed is:

1. An apparatus for detection of foreign bodies in a material, comprising:
    a first antenna device for transmitting electromagnetic signals in the microwave range, said signals comprise at least two signals at different frequencies;
    a second antenna device for receiving signals originating from said first antenna, said received signals, at least partially, pass through said material;
    means for measuring at least amplitude and phase information of said received signals for each separate frequency, so as to obtain a plurality of parameter values;
    means for comparing each parameter value with the corresponding amplitude and phase information of said transmitted signals, so as to obtain a comparison value for each of said separate frequencies;
    means for analyzing each comparison value based on a predetermined reference value, which predetermined reference value is accessible to said apparatus; and
    means for emitting a signal when said comparison value differs a predetermined amount from said predetermined reference value.

2. The apparatus for detection of foreign bodies according to claim 1, wherein each predetermined reference value is derived from comparing said amplitude and phase information of said transmitted signal with a parameter value of a received reference signal for each of said separate frequencies, where said received reference signal, at least partially, has passed through a reference material, said reference material being without any foreign bodies.

3. The apparatus for detection of foreign bodies according to claim 1, wherein each predetermined reference value is derived from comparing said amplitude and phase information of said transmitted signal with a parameter value of a received reference signal for each of said frequencies, where said received reference signal has been obtained by evaluation of a model of the measurement setup and of the transmission properties of a reference material.

4. The apparatus for detection of foreign bodies according to claim 1, wherein said analyzing means compares said amplitude and phase information of each predetermined reference value with each received signal at the separate frequencies.

5. The apparatus for detection of foreign bodies according to claim 1, wherein said amplitude and phase information comprises any of the group consisting of: damping, signal runtime, signal delay time, signal velocity and complex S parameter.

6. The apparatus for detection of foreign bodies according to claim 1, wherein said apparatus is adaptable for on-line detection.

7. The apparatus for detection of foreign bodies according to claim 6, wherein said apparatus is provided with conveyor means for transporting said material past said first and second antenna.

8. The apparatus for detection of foreign bodies according to claim 1, wherein said apparatus has a gap between said first and second antenna in an open structure, whereby a production line may be placed in said gap.

9. The apparatus for detection of foreign bodies according to claim 1, wherein said predetermined reference value is stored in a memory within said apparatus.

10. A method for detection of foreign bodies in a product comprising:
    transmitting electromagnetic signals from a first antenna device, said transmitted electromagnetic signals being in the microwave range, said signals comprise at least two signals at different frequencies;
    receiving signals in a second antenna device originating from said signals transmitted from said first antenna device, where said received signals, at least partially, have passed through said product;
    storing predetermined reference values comprising amplitude and phase information for each transmitted separate frequency in a memory;
    measuring at least amplitude and phase information of said received signals for each separate frequency, so as to obtain parameter values;
    comparing the parameter values with the corresponding amplitude and phase information of said transmitted signals, so as to obtain a comparison value for each of said frequencies;
    analyzing each comparison value using one of said predetermined reference values from said memory; and
    emitting a signal when said comparison value differs a predetermined amount from said predetermined reference value.

11. The method for detection of foreign bodies in a product according to claim 10, wherein the method further comprises:
    obtaining each predetermined reference value from comparison of said amplitude and phase information of said transmitted signal with a parameter value of a received reference signal for each of said frequencies, where said received reference signal, at least partially, has passed through a reference product, said reference product being without any foreign bodies.

12. The method for detection of foreign bodies in a product according to claim 10, wherein the method further comprises:
    obtaining each predetermined reference value from comparison of said amplitude and phase information of said transmitted signal with a parameter value of a received reference signal for each of said frequencies, where said received reference signal has been obtained by evaluation of a model of the measurement setup and of the transmission properties of a reference product.

13. The method for detection of foreign bodies in a product according to claim 10, wherein the step of analyzing each comparison value is performed by comparing amplitude and phase information of each received signal with a corresponding predetermined reference value.

14. An apparatus for detection of changes in material properties and contents in a product, comprising:

a first antenna device for transmitting electromagnetic signals in the microwave range, said signals comprise at least two signals at different frequencies;

a second antenna device for receiving signals originating from said first antenna, said received signals, at least partially, pass through said product;

means for measuring at least amplitude and phase information of said received signals for each separate frequency, so as to obtain parameter values;

means for comparing each parameter value with the corresponding amplitude and phase information of said transmitted signals, so as to obtain a comparison value for each of said separate frequencies;

means for analyzing each comparison value based on a predetermined reference value, which predetermined reference value is accessible to said apparatus; and means for emitting a signal when said comparison value differs from a predetermined amount from said predetermined reference value.

15. The apparatus for detection of changes in material properties and contents in a product according to claim 14, wherein each predetermined reference value is derived from comparing said amplitude and phase information of said transmitted signal with a parameter value of a received reference signal for each of said frequencies, where said received reference signal, at least partially, has passed through a reference product, said reference product having a desired material property and content.

16. The apparatus for detection of changes in material properties and contents in a product according to claim 14, wherein each predetermined reference value is derived from comparing said amplitude and phase information of said transmitted signal with a parameter value of a received reference signal for each of said frequencies, where said received reference signal has been obtained by evaluation of a model of the measurement setup and of the transmission properties of a reference product.

17. The apparatus for detection of changes in material properties and contents in a product according to claim 14, wherein said analyzing means compares said amplitude and phase information of each predetermined reference value with each received signal at the separate frequencies.

18. The apparatus for detection of changes in material properties and contents in a product according to claim 17, wherein said amplitude and phase information comprises any of the group consisting of: damping, signal runtime, signal delay time, signal velocity and complex S parameter.

19. The apparatus for detection of changes in material properties and contents in a product according to claim 14, wherein said apparatus is adaptable for on-line detection.

20. The apparatus for detection of changes in material properties and contents in a product according to claim 14, wherein said apparatus has a gap between said first and second antenna in an open structure, whereby a production line may be placed in said gap.

21. The apparatus for detection of changes in material properties and contents in a product according to claim 19, wherein said apparatus is provided with conveyor means for transporting said product past said first and second antenna.

22. The apparatus for detection of changes in material properties and contents in a product according to claim 14, wherein said predetermined reference value is stored in a memory within said apparatus.

23. A method for detection of changes in material properties and contents in a product comprising the steps of:

transmitting electromagnetic signals from a first antenna device, said transmitted electromagnetic signals being in the microwave range, said signals comprise at least two signals at different frequencies;

receiving signals in a second antenna device originating from said signals transmitted from said first antenna device, where said received signals, at least partially, have passed through said product;

storing predetermined reference values comprising amplitude and phase information for each transmitted different frequency in a memory;

measuring at least amplitude and phase information of said received signals for each frequency, so as to obtain parameter values;

comparing the parameter values with the corresponding amplitude and phase information of said transmitted signals, so as to obtain a comparison value for each of said frequencies;

analyzing each comparison value using one of said predetermined reference values from said memory; and emitting a signal when said comparison value differs a predetermined amount from said predetermined reference value.

24. The method for detection of changes in material properties and contents in a product according to claim 23, wherein the method further comprises the step of obtaining each predetermined reference value from comparison of said amplitude and phase information of said transmitted signal with a parameter value of a received reference signal for each of said frequencies, where said received reference signal, at least partially, has passed through a reference product, said reference product having a desired material property and content.

25. The method for detection of changes in material properties and contents in a product according to claim 23, wherein the method further comprises the step of obtaining each predetermined reference value from comparison of said amplitude and phase information of said transmitted signal with a parameter value of a received reference signal for each of said frequencies, where said received reference signal has been obtained by evaluation of a model of the measurement setup and of the transmission properties of a reference product.

26. The method for detection of changes in material properties and contents in a product according to claim 23, wherein the step of analyzing each comparison value is performed by comparing amplitude and phase information of each received signal with a corresponding predetermined reference value.

* * * * *